(12) United States Patent
Gamble

(10) Patent No.: US 7,109,173 B1
(45) Date of Patent: Sep. 19, 2006

(54) TRANSPORT OF NUCLEOTIDES, OLIGONUCLEOTIDES AND POLYNUCLEOTIDES INTO THE CYTOPLASM AND NUCLEUS OF CELLS BY PEPTIDES

(76) Inventor: Wilbert Gamble, 4115 NW. Dale Dr., Corvallis, OR (US) 97330

( * ) Notice: Subject to any disclaimer, the term of this patent is extended or adjusted under 35 U.S.C. 154(b) by 0 days.

(21) Appl. No.: 11/052,388

(22) Filed: Feb. 7, 2005

Related U.S. Application Data

(60) Provisional application No. 60/553,648, filed on Mar. 16, 2004.

(51) Int. Cl.
*A61K 47/42* (2006.01)

(52) U.S. Cl. .................................................. 514/21

(58) Field of Classification Search ................ None
See application file for complete search history.

(56) References Cited

U.S. PATENT DOCUMENTS

| | | |
|---|---|---|
| 6,617,438 B1 | 9/2003 | Beigelman et al. |
| 6,620,805 B1 | 9/2003 | Takle et al. |
| 6,673,611 B1 | 1/2004 | Thompson et al. |
| 6,790,641 B1 | 9/2004 | Schauber |
| 6,825,006 B1 | 11/2004 | Baum et al. |
| 6,828,149 B1 | 12/2004 | Freier |

OTHER PUBLICATIONS

Hrycyna et al. Mol. Cell. Bio. 1990; 10: 5071-76.*
Kabouridis, PS. Trends Biotech. 2003; 21: 498-503.*
Lindgren et al. 2000 ; Trends. Pharmacol. Sci. 21: 99-103.*
Schwarze et al. Trends Cell biol. 2000; 10: 290-5.*
Taylor et al. EMBO J. 2003; 22: 5963-74.*
Gupta et al. 2005; Adv. Drug Deliv. Rev. 2005; 57: 637-51.*
Wolfe et al. (J. Biol. Chem. 1989; 264(7): 4157-4162).*
Ambion TechNotes 10(1) siRNA Expression Vector with Selectable Markers, article found on-line Dec. 16, 2004.

* cited by examiner

*Primary Examiner*—Daniel M. Sullivan
*Assistant Examiner*—Guy Guidry
(74) *Attorney, Agent, or Firm*—Lori M. Friedman

(57) ABSTRACT

The invention discloses the discovery of naturally occurring peptides that contain fatty acyl and prenyl moieties which permit the transfer of nucleotides, oligonucleotides, and polynucleotides into the cytoplasm and nucleus of cells. Their intrinsic properties cause them to tightly bind to nucleotides. This indicates that they might serve as nucleotide transporters. Experiments demonstrated that they permitted the transfer of nucleotides and polynucleotides into the cytoplasm and nucleus of cells. The peptides, due to their ability to transport ribonucleic acids into cells, can be employed in gene silencing by RNAi (ribonucleic acid interference) and antisense therapy. Among the ailments thought to benefit are: atherosclerosis by regulating cholesterol metabolism, cancer and similar diseases by delivering nucleic acids in chemotherapy. The peptides, due to their ability to transport ribonucleic acids into cells, can be employed in gene silencing.

1 Claim, No Drawings

TRANSPORT OF NUCLEOTIDES, OLIGONUCLEOTIDES AND POLYNUCLEOTIDES INTO THE CYTOPLASM AND NUCLEUS OF CELLS BY PEPTIDES

RELATED PATENT APPLICATIONS

This is a utility patent application based on U.S. provisional patent application Ser. No. 60/553,648 filed Mar. 16, 2004

BACKGROUND OF THE INVENTION

1. Field of the Invention

The present invention relates to compositions and methods for the use of such composition and solution for delivering substances into the cytosol and nucleus of living cells. More specifically, the compositions are peptides that transport nucleotides, oligonucleotides and polynucleotides into the cytoplasm and nuclei of cells.

2. Background and Related Art

In the course of biological research and certain medical procedures it is desirable to introduce a variety of substances into the cytosol of living eukaryotic cells. However, most hydrophilic substances, including many drugs, antisense and antigene oligos, RNAs, DNAs, peptides, proteins, carbohydrates, and combinations thereof, enter eukaryotic cells primarily via endocytosis and are subsequently sequestered or degraded in lysosomes, with little or no intact substance achieving the desired entry into the cytosol of the cells.

One of the diseases in which applicant is researching is coronary heart disease. Coronary heart disease is caused by the atherosclerotic narrowing of the coronary arteries affecting nearly 14 million persons in the United States. Approximately 480,000 deaths in 1995 were caused by the disease and it is the leading cause of death in the United States today. One of the established causes of atherosclerosis is elevated cholesterol levels and elevations of the major protein responsible for carrying cholesterol-apolipoprotein B (apoB). In treating atherosclerosis and other diseases, a difficult and yet unsolved problem is an effective way to deliver a drug to the cytosol and nuclear organelles in living organisms.

Double-stranded RNA interference (RNA-i) is a process wherein a ribonucleic acid is used to interfere with the expression of a certain gene. The RNAi is used to silence a particular gene by inhibiting the formation of a protein at the post-translation step of the process.

In order to silence a particular gene, the RNAi must enter the cell. There are several reagents and mechanisms by which this entry, called transfection, occurs. Examples of some known methods and reagents used in transfection include liposomes, small interfering RNAs (siRNAs), viral vectors (plasmids), RNA viruses, adeno viruses, lentil viral vectors, electrodeposition, and various custom-synthesized proprietary compounds.

Relevant background material is found in several scientific research articles. Among them are two articles published in the journal *Nature*; namely an "insight" review article entitled "RNA interference", by Gregory J. Hannon in Volume 418, Jul. 11, 2002. This article discusses double-stranded RNA interference (RNA-i), cultivated as a means to manipulate gene expression experimentally and to probe gene function on a whole genome scale.

Biotech companies such as Ambion publish "TechNotes" to promote transfection of various siRNA expression vectors. Three brief articles appearing in the Ambion TechNotes newsletter include: A "How to" for New Users", appearing in Volume 11, Number 5, 2004, "Delivering siRNA's to Difficult Cell Types, Volume 11, Number 3, November 2004, and siRNA Libraries Targeting Important Human Gene Classes, Volume 11, Number 5, 2004.

Several patents have been issued that include the use of viral vectors. They include U.S. Pat. No. 6,790,641 to Schauber et al, where the inventors provide a retroviral gene delivery system used to produce recombinant retroviral particles for transgene delivery. In U.S. Pat. No. 6,620,805 to Takle et al relates to porphyrins which protect the compound being delivered and delivers it to certain cell and tissue types. Porphryns are not categorized as peptides or proteins, but are a class of red-pigmented compounds with a cyclic tetrapyrollic structure in which the four pyrrole rings are joined through their alpha-carbon atoms by four methane bridges. The porphyrins form the active nucleus of chlorophylls and hemoglobin. Neither of these patents discusses the naturally occurring peptides that are the subject of this invention.

In U.S. Pat. No. 6,673,611 Thompson et al describe chemically-modified nuclei acid molecules; it is not about transport per se, as the novel nucleic acid molecules are not transport agents. In U.S. Pat. No. 6,617,438 to Beigelman et al the nucleic acids of interest have enzymatic activity and also are not transport agents.

In U.S. Pat. No. 6,828,149 Freier relates to antisense compounds and not transport agents or vectors. In U.S. Pat. No. 6,825,006 Baum et al again the modified nucleic acids are not transport agents.

In the present invention, Applicant is introducing a variety of nucleotides and nucleic acids into the cytosol of living eukaryotic cells. Applicant's invention deals with naturally occurring peptides that facilitate the transfer of nucleotides and nucleic acids into the nucleus and cytoplasm of cells.

The discovery of peptide, nucleotide and nucleic acid transporters that transport nucleic acids into the nucleus and cytosol of cells will permit the delivery of a variety of pharmaceuticals. Among the ailments thought to benefit from this invention is atherosclerosis, by regulating cholesterol metabolism. Cancer and other ailments will benefit from the delivery of nucleic acids as taught by the instant invention during chemotherapy. The peptides, due to their ability to transport ribonucleic acids into cells, can be employed in gene silencing by RNAi (ribonucleic acid interference) and antisense therapy.

SUMMARY OF THE INVENTION

It has been surprisingly found during the course of research on the etiology of atherosclerosis that certain peptides of the chemical structure:

$NH_2CHR_1CO(HNCHRCO)_nHNCHR_{n+2}COOH$ are effective in the delivery of nucleotides into cells. The peptides are linear.

The number of residues is represented by the letter n. In this invention, R represents the side chains of the amino acids. The peptides contain fatty acyl- and prenyl-moieties and are effective nucleotide transporters in living cells. The intrinsic properties of these modified peptides cause them to tightly bind to nucleotides. Additional experiments demonstrated that they permitted the transfer of nucleotides and polynucleotides into the cytoplasm and nucleus of cells.

An object of the present invention is to provide such delivery compositions which afford delivery of desired substances into the cytosol and nucleus of living cells. This is accomplished by the use of said fatty acyl- and prenyl-containing peptides wherein the peptides are oligo- and polypeptides that occur naturally in the aorta, macrophages and smooth muscle cells of living organisms.

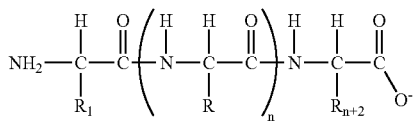

Diagrammatic representation of peptides

A further object of this invention is to provide a method for the delivery of nucleotides and the like into the cytosol and nuclear organelles in a patient. The method transfers nucleotides, oligonucleotides, and polynucleotides to the cytoplasm and nucleus of a cell. The details of such modifications will be further described and presented, along with experimental details, in the detailed description that follows.

DETAILED DESCRIPTION OF PREFERRED EMBODIMENTS

In research efforts of the pharmaceutical industry to deliver effective drugs into the body to fight disease, one of the most difficult problems is to find a compound that will deliver oligonucleotides into the cytosol and nuclear organelles in patients. In research seeking the etiology of atherosclerosis, the mechanism of the deposition of cholesterol in aorta, smooth muscle cells and macrophages peptides were discovered. They were covalently labeled with prenyl and fatty acyl moieties.

The delivery compounds are peptides composed of alpha-amino acids in amide linkages which contain linear, medium chain fatty acid acyl moieties in amide linkages and prenyl moieties in thioether linkages.

$$NH_2CHR_1CO(HNCHRCO)_nHNCHR_{n+2}COOH$$

The peptides are linear. The number of residues is represented by the letter n which varies. The peptides are comprised of a plurality of amino acids and are covalently linked by amide (peptide) bonds.

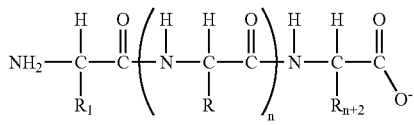

Diagrammatic representation of peptides

The peptides had strong affinity for nucleotides and were shown to transport nucleotides across anion exchange membranes. They were shown to facilitate the transfer of polynucleotides and nucleotides to the cytoplasm and nucleus. The amino acid compositions and masses of the peptides were determined and a sequence deduced for one of them.

The structure below, which uses three-letter abbreviations for amino acids, is representative of peptides with demonstrated activity as a nucleotide transporter:

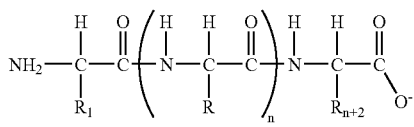

Diagrammatic representation of peptides

HIS-GLY-VAL-CYS-PHE-ALA-SER-MET
|
S-Farnesy

The peptides were isolated during continuing academic research efforts. Their intrinsic properties caused them to tightly bind to nucleotides, in the course of their isolation, characterization and purification. The chemical properties of these peptides suggested that they might serve as nucleotide transporters. Additional experiments demonstrated that they permitted the transfer of nucleotides and polynucleotides into the cytoplasm and nucleus of cells.

Masses observed for the peptides were 820.1, 1038.1, 1226.7, 1268.5, and 1478.6. The mass spectra analysis and amino acid composition has permitted the deduction of the preferred peptide sequence shown above.

Research results show that these peptides occur naturally in the aorta and in macrophages. They contain lipid moieties and are soluble in water. They traverse ion exchange membranes, permit the transfer of polynucleotides and mononucleotides to the cytoplasm and nucleus of cells, and they can be isolated easily and inexpensively. The following details demonstrate that the cells grown in culture when incubated with mononucleotides, oligonucleotides and polynucleotides in the presence of the peptides permitted the uptake of various desired compounds. This was demonstrated by isolation from cells after treatment, quantitative biochemical analysis, and microscope spectrophotometry.

EXPERIMENTAL DETAILS

The following details are a description of the isolation, detection and identification of prenyl and fatty acyl proteins.

I: Preparation of microsomal supernatant—Aortas from cattle 2–3 years old were obtained immediately after killing and chilled on ice. The adventitia and excess fat are removed with scissors. Then the aorta samples were rinsed with cold distilled water. Only the portion below the bifurcation of the aorta (12–14 inches in length) was used. Plastic gloves were worn during the process to prevent contamination of the preparation. Aortas samples were cut into small strips with scissors. The strips were then homogenized in a Waring Blender at high speed with an equal weight of cold 0.1 M pH 7.0 phosphate nicotinamide buffer (0.1 M phosphate, 0.03 M nicotinamide and 0.006 M $MgCl_2$). The resulting homogenate was then centrifuged at 3000 RPM using a GSA rotor in a Servall refrigerated centrifuge at 4° C. for 40 minutes. The supernatant fluid was then decanted and can be kept frozen over a period of several months without significant loss of activity. The crude preparation was centrifuged at 60,000×g in a Beckman Model L5-65 in a 30S rotor for 120 minutes. The resulting clear microsomal supernatant preparation was used within a few hours after centrifugation. This protocol constitutes the standard protocol. Standard protocol used in these preparations for isolation of the 60,000×g post mitochondrial preparation which contains the peptides.

The appropriate conditions for synthesis of lipids by the aorta preparation were made using a Dual homogenizer, meat grinder, Potter Elvehjem or a Tekmar homogenizer. The best results were obtained with the Waring Blender. The phosphate buffer employed gave the best results compared to sucrose and tris-hydroxymethyl amino methane hydrochloride. ATP is absolutely required, NAD and NADPH (as $NADP+Glucose-6-PO_4$) are required for maximum incorporation. In this procedure, incorporation defined as the mevalonate into cholesterol and prenyl derivatives Maximum incorporation was obtained after 175–200 minutes incubation. There was low observable acetothiokinase activity in the 60,000×g supernatant and hence low incorporation of acetate per se. The homogenate was centrifuged at 480×g, 9750×g, and 20,200×g to obtain supernatant fractions. Each of these preparations had less activity than the 60,000×g supernatant. In some experiments the fractions from the centrifugation at lower speeds were inactive. The high ATPase and phophatase activity in these preparations are thought to be responsible for the lower activity.

II: Incubation—Incubations were performed in 125 ml Erlenmeyer flasks and 250 ml flasks in preparative experiments. Each flask contained 16.9 μmoles ATP, 6.2 μmoles NAD⁺, 5 ml microsomal supernatant, and 2.5 ml 0.1 M pH 7.0 phosphate nicotinamide buffer in a total volume of 10.5 ml. The volumes were increased 10 fold in preparative experiments and reduced 10 fold in microanalytical experiments. Each flask was swirled in a stream of oxygen (95% $O_2$. 5% $CO_2$) for 15 seconds, stoppered and sealed tightly. The flasks were then incubated in Research Specialties oscillating water bath at 37° C. for 2 hours and 50 minutes. After incubation was complete, the incubation solution of post mitochondrial supernatant undergoes an extraction with petroleum ether. The extraction produces two fractions; one is the petroleum ether extract and the other is the aqueous extract. The following procedures were followed:

III: Protein Precipitation—The incubation solution is brought to 80% concentration of ethanol by the addition of 95% ethanol. The mixture was placed in a −40° C. freezer overnight. The mixture was centrifuged at 3,000 rpm in a Sorvail centrifuge at 4° C. in a GSA rotor for one hour. The supernatant was removed and saved (for analysis of water soluble acids). The precipitate was washed with (10 ml) 95% ethanol by centrifuging in 30 ml corex tubes in a SS 34 rotor at 5,000 rpm for 20 minutes. The procedure was repeated with 100% ethanol. The supernatants were saved as before. The precipitate was dried, weighed, and saved for analysis.

IV: Dialysis of Protein—346 mg of protein precipitate was dissolved in 10 ml of distilled water. The solution was centrifuged at 10,000 rpm in a SS34 rotor in a Sorvail centrifuge at 4° C. in corex tubes for 15 minutes. The supernatant was used for dialysis. It was dialyzed for 48 hours against water. The dialysate and dialysant were saved. The dialysant was concentrated in a Buchi evaporator under vacuum.

Separation procedures, as outlined in the following flow chart, were then followed:

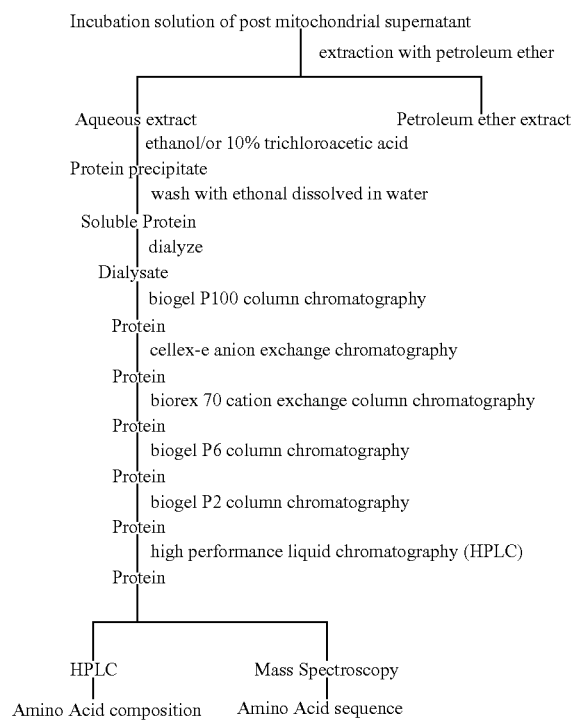

The following are the details of the separation procedures outlined above:

Bio Gel P100 Column Chromatography—A Bio Gel P100 column of 28 cm×2.5 cm was prepared. The column was washed with pH 7.0 0.1M, 0.006 M $MgCl_2$ buffer until there was no ultra violet absorbance at 280 nM. The protein sample was dissolved in 10 ml of distilled water. 7.6 ml of the sample was placed on the column followed by 7.6 ml of water. The column was eluted with pH 7.0 0.1 M phosphate buffer. Fractions of 6.0 ml at 4.7 minute per fraction were collected (47 tubes). Aliquots were counted by means of a Beckman liquid scintillation counter using Aquosol as the fluor. The absorbance at 280 nM and 260 mM were determined and the ultra violet spectrum of each fraction.

Bio Gel P6 Column Chromatography—A Bio Gel P2 column of 25.5 cm×1:0 cm was prepared. The column was washed with pH 7.0 0.1 M phosphate 0.006 M $MgCl_2$ buffer. The protein sample was dissolved in 3 ml of $H_2O$ and applied to the column. Fractions of 6.5 ml per 5 minutes were collected. The ultra violet spectra of each fraction and the 280 nM, 260 nM absorbencies were performed.

Bio Gel P2 Column Chromatography—A 1.5×33 cm column was prepared. The protein solution, 2 ml, was placed on the column followed by 2 ml of water 6.5 ml/8 minutes. Fractions were eluted with water. The ultra violet absorption spectra and absorbencies at 250, 260, 280 nM were determined using a Hewlett-Packard diode array spectrophotometer.

Bio Rex-70 Column Chromatography—A 1.3 cm×20 cm cation exchange column was prepared using Bio-Rad 70. The column was washed with 1 M LiCl until there was no ultra violet absorbance in the eluant. A 3.1 ml aliquot of the protein solution was placed on the column followed by 2 ml of water. Then using a linear gradient in a Buchler Varigrad from zero to 1 M LiCl, 6.5 ml fractions were collected. Aliquots were counted by means of a Beckman LSC scintillation counter in Aquosol fluor. The ultraviolet spectra and absorbances at 250, 260, and 280 nM were determined.

Cellex-E Column Chromatography—An anion exchange column 1×20 cm was prepared using Bio Rad Cellex-E. The column was washed with 1 M LiCl until it was clear of ultra violet absorbing material. It was then washed with water to remove excess LiCl. 2 ml of the protein solution was placed on the column followed by 2 ml of water.

The fractions were eluted with a linear gradient of LiCl from 0 to 1 M LiCl. using a Buchler Varigrad. Fifty fractions of 5.9 ml per 6 minutes were collected. The ultraviolet spectra and absorbance at 260, 280, and 250 nM were determined. Aliquots were counted for radioactivity by means of a Beckman LSC liquid scintillation counter, using Aquasol as the fluor.

V. Methods and Materials for Quantification of the Degree of Transport of Nucleotides 1. Analysis of control cells stopped at zero time gives the original content of nucleotides of interest.

2. Analysis of control cells stopped after 24 hour incubation gives the change in nucleotide content during the 24 hr period. That is, 24 hr content of control cells minus zero time control cells nucleotide content equals net change.

3. Analysis of nucleotide treated cells at zero time incubation gives the initial content and/or bound nucleotides.

4. Analysis of nucleotide treated cells at 24 hour time gives the amount present after 24 hours.

5. 24 hour content minus zero time content gives the net change in nucleotide content.

6. The net content of the 24 hr nucleotide treated cells minus the zero time content of nucleotides gives the amount transported by the peptides.

7. The net values are previously corrected for the amount in the original media and wash for the treated cells.

Fibroblasts cells were incubated for 24 hrs with and without fetal calf serum. Cells harvested at zero time served as controls. They were subjected to all of the analyses performed on experimental cells. Cells were harvested as described in 'section V. Methods and Materials'. Macrophages were treated the same as previously described for fibroblasts except human serum was used in place of fetal calf serum and they were not cultured without serum. Cells were incubated with predetermined amounts of nucleotides with and without peptide Incubations were stopped at zero time and 24 hrs. The media harvested at zero and 24 hrs was saved for analysis for peptides and nucleotides.

Cells were washed and harvested as described previously. The wash was saved for analysis of peptides and nucleotides. Some cells were sonicated and aliquots analyzed for radioactivity by a liquid scintillation spectrometer (counter). The results indicate the amount of peptide retained by the cells. Spectrophotometric analysis quantifies the amount of nucleotide retained.

VI: Extraction of lipids—The non-saponifiable lipids and free fatty acids were extracted using petroleum ether (30–60° C.). Neutral lipids were extracted with petroleum ether without prior saponification. It should be noted that when mevalonate-2-$^{14}$C was employed as the substrate, extraction by the Bligh-Dyer method and the Folch method resulted in the extraction of mevalonate. The latter two methods, when used, necessitate extensive chromatographic separation of mevalonate from the phospholipids and neutral lipids. Except to demonstrate the presence of radioactivity in the phospholipids, the latter two extraction procedures were not be used. Control experiments in which the reaction was stopped at zero time and in which the enzyme preparation is omitted show no radioactivity is extracted when the usual incubation, saponification, and isolation procedures were performed.

The method for the delivery of polynucleotides, oligonucleotides and polynucleotides in cells into the cytosol and nucleus of cells is thus accomplished in the instant invention by a) Isolating the peptides then b) incubating the peptide sample with predetermined amounts of nucleotides with and without peptides. After this, the nucleotides are transferred into the cells. Cells were treated with homopolymers in the presence and absence of the peptides. Uptake was determined as described under Methods and Materials, above. The polynucleotides were quantified spectrophotometrically and by single cell fluorescence analysis using syto-13 (Molecular Probes). Quantitative measurements are presented in Tables 2,3, and 4 below. The results show that homopolymers of nucleic acids are taken up by the cells.

TABLE 2

Uptake of Homopolymers by Fibroblasts:
Fluorescence Relative Intensity

| Polynucleotide | Experimental | Control |
| --- | --- | --- |
| Polyadenylic acid | 27.4 ± 7.5 (n = 23) | 11.7 ± 3.8 (n = 22) |
| Polycytidylic acid | 14.9 ± 1.6 (n = 14) | 3.3 ± 0.6 (n = 14) |
| Polyguanylic acid | 39.2 ± 9.5 (n = 17) | 13.1 ± 3.1 (n = 24) |
| Polyuridylic acid | 16.8 ± 4.6 (n = 23) | 4.4 ± 1.3 (n = 22) |

Fibroblasts were cultured as described under V.Methods and Materials. Cells were stained with syto-13 (Molecular Probes). Single cell fluorescence analysis was performed using a Zeiss microscope photometer. Values are relative intensity ±standard deviation. N=number of cells.

Table 3 demonstrates the uptake of polynucleotides in the presence and absence of peptides by human fibroblasts

TABLE 3

| | Peptides | | Without Peptides | |
| --- | --- | --- | --- | --- |
| Polynucleotide | Absorbance | μ grams | Absorbance | μ grams |
| Polyadenylic acid | 0.200 ± 0.101 | 252 | 0.047 ± 0.025 | 59 |
| Polycytidylic acid | 0.209 ± 0.028 | 380 | 0.052 ± 0.031 | 94 |
| Polyguanylic acid | 0.444 ± 0.058 | 1160 | 0.223 ± 0.084 | 580 |
| Polyuridylic acid | 0.370 ± 0.07 | 436 | 0.071 ± 0.013 | 82 |

The cells were cultured as described under Methods, above. The experiments were stopped at zero time and 24 hours. Values are obtained by subtracting initial zero time values from those of 24 hrs. Values are ±standard deviation. Absorbance measured spectrophotometrically at 260 nM.

Table 4 depicts the determination of cellular loci of administered polynucleotides

TABLE 4

| | Nuclear Fraction | | Microsomal Fraction | |
| --- | --- | --- | --- | --- |
| Polynucleotide | *Absorbance | μ grams | *Absorbance | μ grams |
| Polyadenylic acid | 0.265 ± 0.061 | 59.1 | 0.242 ± 0.038 | 155 |
| Polycytidylic acid | 0.254 ± 0.026 | 107.4 | 0.236 ± 0.025 | 153 |
| Polyguanylic acid | 0.354 ± 0.030 | 747.7 | N.D. | N.D. |
| Polyuridylic acid | 0.326 ± 0.050 | 246.1 | 0.313 ± 0.030 | 186 |

*Absorbance equals observed values. N.D. = not detected.

Cells were cultured and treated as described under Methods, above. Cells were subjected to differential centrifugation. μ grams calculated after correction of values by subtracting zero time control values from experimental values. No significant absorbances of nucleotides were detected in the experimental samples in the mitochondrial-lysosomal fraction when zero time control values were subtracted from the experimental values. Absorbance was measured spectrophotometrically at 260 nM.

Thus, the two latter steps of the method described in the claims, involving transferring a peptide to bind tightly with a target nucleotide into the cell by binding said peptide across an anion exchange membrane; and facilitating the transfer of nucleotides to the cytoplasm and nucleus of the patient's cells were shown to be viable. In a preferred embodiment of this invention, the target cells are smooth muscle cells and macrophages which are found in atheromatous plaques. The plaques are a focal thickening of the intima caused by proliferation of smooth muscle cells.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A peptide composition consisting of SEQ ID NO: 1 wherein S-Farnesyl is attached to the CYS that facilitates the transport and entry of nucleotides, oligonulceotides and polynucleotides into the cytoplasm and nucleus of human smooth muscle cells, macrophages and fibroblasts.

* * * * *

```
                           SEQUENCE LISTING

<160> NUMBER OF SEQ ID NOS: 1

<210> SEQ ID NO 1
<211> LENGTH: 8
<212> TYPE: PRT
<213> ORGANISM: bovine

<400> SEQUENCE: 1

His Gly Val Cys Phe Ala Ser Met
1               5
```